(12) United States Patent
Paranjpe

(10) Patent No.: US 6,899,668 B2
(45) Date of Patent: May 31, 2005

(54) AIRBORNE PATHOGEN ISOLATION SYSTEM AND METHOD

(76) Inventor: Amod Prabhakar Paranjpe, 1044 McKnight Rd., St. Louis, MO (US) 63117

( * ) Notice: Subject to any disclaimer, the term of this patent is extended or adjusted under 35 U.S.C. 154(b) by 0 days.

(21) Appl. No.: 10/360,891

(22) Filed: Feb. 7, 2003

(65) Prior Publication Data

US 2004/0158120 A1 Aug. 12, 2004

(51) Int. Cl.$^7$ ............................................. A61G 10/00
(52) U.S. Cl. ........................ 600/21; 128/849; 454/56; 55/385.2
(58) Field of Search ...................... 600/21–22; 454/56, 454/237; 55/385.2

(56) References Cited

U.S. PATENT DOCUMENTS

| | | | |
|---|---|---|---|
| 2,218,296 A | 10/1940 | Perras | 132/73 |
| 2,260,687 A | 10/1941 | Lasha | 34/202 |
| 2,490,019 A | 12/1949 | Elliot | 34/202 |
| 3,930,320 A | 1/1976 | Henderson | 34/202 |
| 4,038,974 A | 8/1977 | Pieklenrood | 128/1 R |
| 4,063,913 A | 12/1977 | Kippel et al. | 55/274 |
| D279,034 S | 5/1985 | Putney | D28/56 |
| D299,559 S | 1/1989 | Wong | 28/58 |
| 4,967,775 A | 11/1990 | Kaiser | 132/73 |
| 5,054,480 A | 10/1991 | Bare et al. | 128/201.25 |
| 5,085,234 A | 2/1992 | Silverman | 132/73 |
| 5,103,845 A | 4/1992 | Matthews | 132/73 |
| 5,112,373 A * | 5/1992 | Pham | 96/142 |
| 5,139,546 A | 8/1992 | Novobilski | 55/316 |
| 5,336,128 A | 8/1994 | Birdsong | 454/56 |
| 5,396,904 A * | 3/1995 | Hartigan, Jr. | 128/849 |
| 5,464,029 A | 11/1995 | Rentz | 132/73.5 |
| 5,533,305 A | 7/1996 | Bielecki | 52/79.1 |
| 5,816,906 A * | 10/1998 | Mai | 454/56 |
| 5,918,606 A | 7/1999 | Bilotto | 132/73 |
| 6,309,222 B1 | 10/2001 | Billingsley | 433/229 |

FOREIGN PATENT DOCUMENTS

| | | | | |
|---|---|---|---|---|
| DE | 100 26 917 | 12/2001 | ......... | A45D/44/02 |
| JP | 11022488 | 8/2000 | ............ | F16P/1/00 |

\* cited by examiner

Primary Examiner—John P. Lacyk
(74) Attorney, Agent, or Firm—Husch & Eppenberger, LLC; H. Frederick Rusche

(57) ABSTRACT

An apparatus for isolating airborne pathogens created during a procedure performed on an individual's extremity includes a transparent, dome-shaped shield having first and second openings therein to allow two individuals to insert their respective extremities into the shield, said first and second openings being located on opposite sides of the shield, and said shield further having a ventilation opening located generally between the first and second openings; an air-cleaning filter located at the ventilation opening; and a fan mounted to the shield and communicating with the ventilation opening and the air-cleaning filter with the filter located adjacent the inlet side of the fan, whereby fumes created during the procedure are directed through the filter.

12 Claims, 3 Drawing Sheets

AIRBORNE PATHOGEN ISOLATION SYSTEM AND METHOD

TECHNICAL FIELD OF THE INVENTION

The present invention relates generally to air quality control devices and, more particularly, to a device for isolating and collecting airborne pathogens produced during cosmetic and medical procedures performed on a human extremity.

BACKGROUND OF THE INVENTION

Finger and toe nail care providers, including manicurists, podiatrists and surgeons, are regularly exposed to hazardous working conditions due to the huge variety of noxious fumes and particles produced during common cosmetic and medical procedures performed on fingernails and toenails. In the manicure and pedicure industry, both the technician and client are routinely exposed to potentially harmful airborne pathogens and contaminants produced by filing and/or grinding the client's nails. Some of the more prevalent contaminants in this industry include ethyl methacrylate, methyl methacrylate, benzyl peroxide, acrylic powder, bond aid, primer, acetone, butyl acetate, toluene, titanium dioxide, and filing dust. Podiatrists and their patients are exposed to a tremendous volume of fungal nail dust and particulate matter, containing known pathogens, such as dermatophytes, non-dermatophytes, yeasts and molds, during common procedures, for example, grinding fungal toenails. Surgeons, surgical staff and their patients are exposed to many of these same pathogens, as well as blood and bodily fluids, during surgeries involving hyfrucation, use of methyl metacrylate, and manual or power irrigation.

Common methods of protecting medical professionals, technicians, patients and clients from exposure to airborne pathogens are generally limited to the use of masks and goggles. These items provide, at best, limited protection for the wearer, while ignoring the inherent risk to the client or patient and other individuals in the area. Furthermore, these items interfere with the care giver's vision and hand/eye coordination, thereby placing the client or patient at additional risk of discomfort or injury.

Common vacuum systems used in these industries do not contain fine airborne particles and dust in an adequate manner, thereby allowing unfiltered dust to permeate the air. In addition, these systems cannot capture larger pieces of debris created by drilling due to the size and velocity of the pieces. This debris forms high speed projectiles that can strike the technician or client in the eye or in other sensitive areas.

Other significantly more complicated protection systems include large and expensive isolation tanks and complex vacuum/ventilation systems. These systems are too expensive for most care givers, are not sufficiently compact for simple table top use, can not be moved to different locations within a facility, and present a frightening appearance to the client or patient. Furthermore, these systems are not easily adaptable to applications within different industries and must be completely redesigned for each application.

An improved airborne pathogen isolation system would preferably be compact, lightweight, portable and affordable and also easily adaptable for use in a variety of industries.

The present invention is directed to overcoming one or more of the problems set forth above.

SUMMARY OF THE INVENTION

An aspect of the present invention is to provide an improved airborne pathogen isolation system capable of minimizing the exposure of clients, patients, technicians, and medical professionals to airborne pathogens produced during common cosmetic and medical procedures.

Another aspect of the present invention is to provide a compact, lightweight, portable, affordable and aesthetically pleasing airborne pathogen isolation system.

Yet another aspect of the present invention is to provide an airborne pathogen system that is easily adaptable for use in a variety of different industries.

In accordance with the above aspects of the invention, there is provided an apparatus for isolating airborne pathogens created during a procedure performed on an individual's extremity that includes a transparent, dome-shaped shield having first and second openings therein to allow the individual to insert his or her extremity into the interior of the shield through the first opening and a care giver to insert a nail care tool or other implement into the interior of the shield through the second opening, said first and second openings being located on opposite sides of the shield, and said shield further having a ventilation opening located generally between the first and second openings; an air-cleaning filter located at the ventilation opening; and a fan mounted to the shield and communicating with the ventilation opening and the air-cleaning filter, with the filter located adjacent the inlet side of the fan, whereby fumes created during the procedure are directed through the filter.

There is also provided a podiatric examination chair incorporating an airborne pathogen isolation system that includes a patient support portion having a seat, a back, a leg support, and means for adjusting said seat, back and leg support; a transparent, dome-shaped shield having first and second openings therein, wherein the individual's extremity is inserted into the interior of the shield through the first opening and a tool to perform the procedure is inserted into the shield through the second opening; and means for detachably connecting the shield to the leg support.

There is further provided a method for isolating airborne pathogens created during a procedure on an individual's extremity that includes the steps of inserting the individual's extremity into a first opening of a transparent, dome-shaped shield having first and second openings and a ventilation opening; inserting a nail care tool into the shield through the second opening; performing the procedure on the individual's extremity with the nail care tool; ventilating air from the interior of the shield with a fan connected with the shield at the ventilation opening; and filtering the air during ventilation with an air-cleaning filter.

These aspects are merely illustrative of the innumerable aspects associated with the present invention and should not be deemed as limiting in any manner. These and other aspects, features and advantages of the present invention will become apparent from the following detailed description when taken in conjunction with the referenced drawings.

BRIEF DESCRIPTION OF THE DRAWINGS

Reference is now made to the drawings which illustrate the best known mode of carrying out the invention and wherein the same reference numerals indicate the same or similar parts throughout the several views.

DETAILED DESCRIPTION

Figure 1:
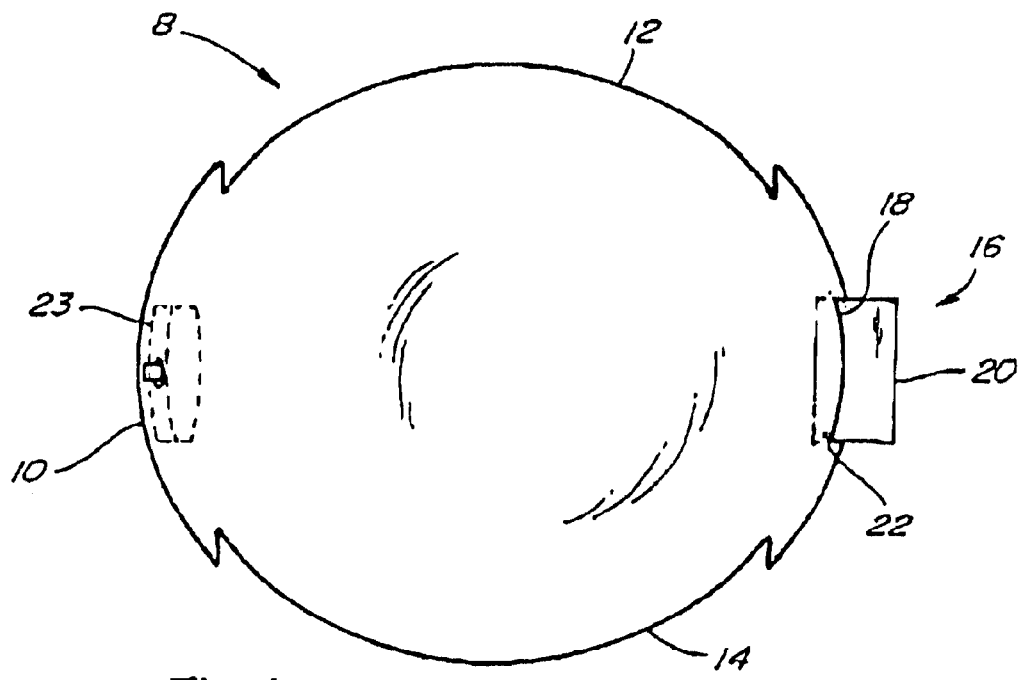
FIG. 1 is a plan view of an airborne pathogen isolation system according to one embodiment of the present invention.
Figure 2:
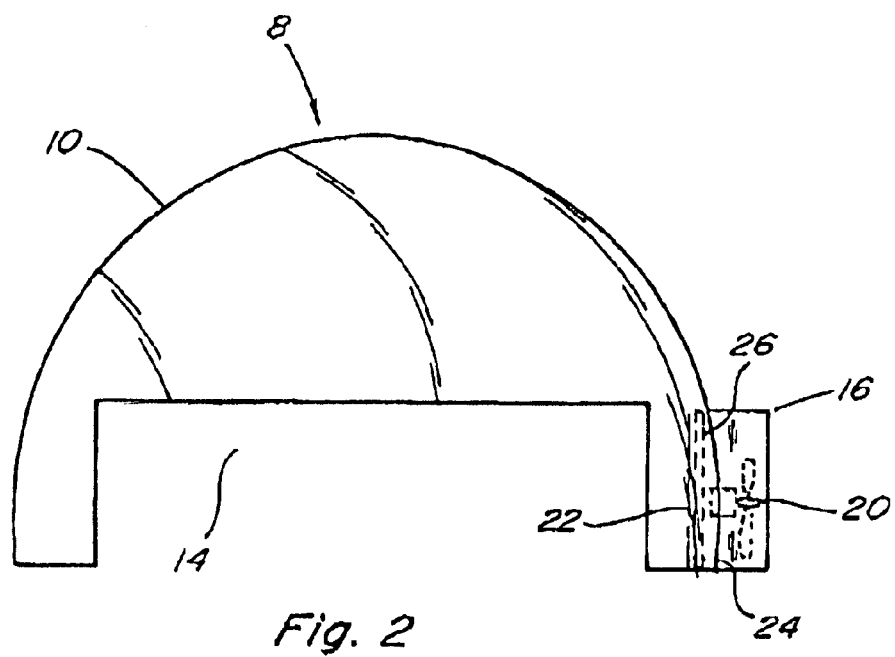
FIG. 2 is a side view of the airborne pathogen isolation system of FIG. 1.
Figure 3:
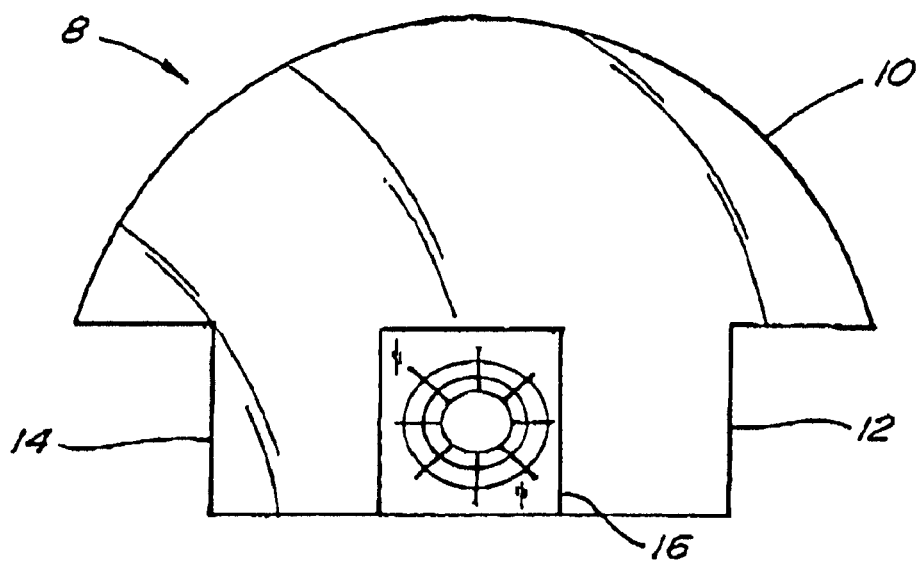
FIG. 3 is an alternative side view of the airborne pathogen isolation system of FIG. 1.

FIGS. 1–3 illustrate a device 8 for isolating and collecting airborne pathogens during cosmetic or medical procedures on human extremities. The device 8 includes a dome-shaped shield 10. The shield 10 has first and second access openings 12, 14 on opposite sides of the shield. The openings 12, 14 are arranged to permit a client/patient to insert an extremity into the interior of the shield from one side while a manicurist, physician or technician inserts their hands and any required instruments into the interior of the shield to perform work on the client's/patient's extremity.

The shield 10 also includes a ventilation system 16 having a ventilation opening 18, a fan 20, and a filter 22. In one embodiment of the device, the filter 22 is attached at the ventilation opening 18 on the interior of the shield 10, while the fan 20 is attached at the ventilation opening on the exterior of the shield 10. In this embodiment, gaskets 24, 26 are preferably positioned between the filter 22 and the shield 10 and between the shield 10 and the fan 20. In an alternate embodiment, both the filter 22 and the fan 20 are positioned at the ventilation opening on the exterior of the shield 10. In this embodiment, the fan 20 and filter 22 may be assembled, installed and removed as a single unit. Advantageously, the ventilation opening 18 is positioned generally between and in close proximity to the first and second access openings 12, 14. This positioning places the ventilation system 16 close to the client's inserted extremity, while preventing the system from obscuring the technician's view into the interior of the shield 10.

In most applications a standard flat or pleated air-cleaning filter is suitable for use with the system. A filtration efficiency of approximately 55% for particles of 0.3 micron diameter is preferred. In these applications, a low-volume fan is preferable due to its quieter performance. However, in an alternate embodiment, a high-efficiency particulate air ("HEPA") filter, capable of obtaining a filtration efficiency of approximately 99% for particles of 0.3 micron diameter is utilized. A higher volume fan is required for this embodiment.

Figure 4:
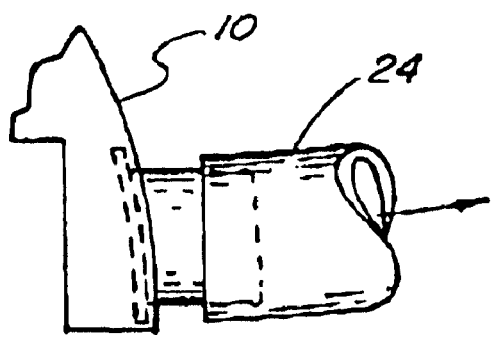
FIG. 4 is a partial side view of an airborne pathogen isolation system incorporating an expandable sleeve for connection to an existing vacuum system.

In an alternate embodiment shown in FIG. 4, an expandable sleeve 24 is connected to the exterior of the shield 10 at the ventilation opening 18. The expandable sleeve 24 allows the connection of a hose from an existing suction system, for example, a vacuum (not shown), to the shield 10. The existing suction system can then perform the ventilation function served by the fan 20 and filter 22 in the preferred embodiment. If the existing suction system does not include a suitable filter, then the filter 22 may be used with the existing suction system.

The shield 10 itself is advantageously constructed of a rigid, transparent material capable of being vacuum formed. Examples of suitable materials include vinyl, polyethylene terephthalate glycol ("PTEG", e.g., Spectar® Copolymer Sheet by Eastman Chemical Co.), acrylic, polyvinyl chloride ("PVC"), acrylonitrile butadiene styrene, and polypropylene. In a preferred embodiment, the shield 10 is approximately ⅛" thick.

Another alternative embodiment of the device 8 includes a reversible fan. During normal isolation operation, the fan will operate to ventilate air out of the shield 10 through the filter 22. However, in applications in which enhanced drying is desired, such as after applying polish to a client's nails following a manicure, the direction of the fan is reversed so that air flows into the enclosed area and around the client's nails.

In yet another alternative embodiment, the device 8 is provided with a small light fixture 23 to enhance the vision of the manicurist or technician into the shield 10. Examples of suitable light fixtures include LED lights, flashlight lights or other low-profile bulbs and fixtures that take up a minimum of room within the shield 10. The light fixture may be either battery powered or have a standard electrical cord. In one advantageous embodiment, the light fixture 23 and fan 20 are powered by the same electrical source, thereby minimizing the electrical complexity of the device and resulting in a further reduction of manufacturing costs.

The above described device has applications in a variety of industries. In the beauty industry, the system would be used to isolate a client's hands or feet during a manicure or pedicure. This application would protect both the technician and client from potentially harmful airborne pathogens and contaminants produced by filing and/or grinding the client's nails. Some of the more prevalent contaminants in this industry include ethyl methacrylate, methyl methacrylate, benzyl peroxide, acrylic powder, bond aid, primer, acetone, butyl acetate, toluene, titanium dioxide, and filing dust. In this application, the compact and lightweight nature of the system would allow it to be easily moved to different manicure/pedicure stations. Furthermore, the relatively low cost of manufacturing the system would in turn likely reduce the retail cost of the system, thus making it affordable to almost any manicurist.

Figure 5:
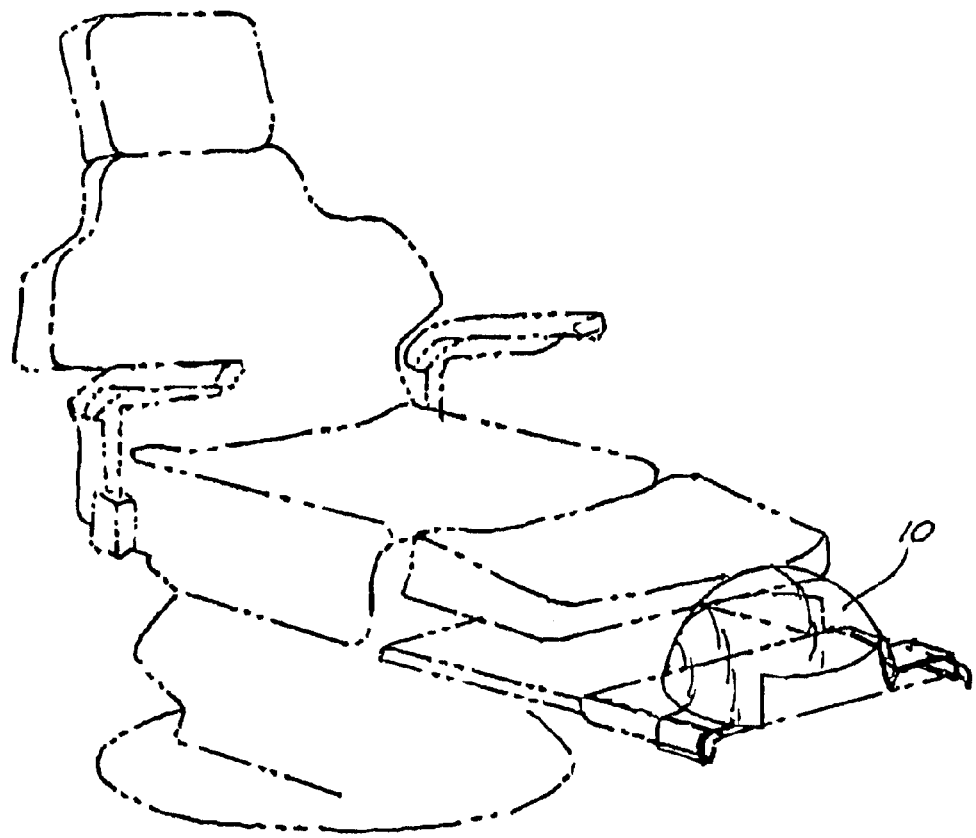
FIG. 5 is a schematic view of a standard podiatric examination chair incorporating an airborne pathogen isolation system.

In the podiatry industry, the system would primarily be used to isolate a patient's feet while grinding fungal toenails. This common procedure creates a tremendous volume of fungal nail dust and particulate matter. A large number of known pathogens, including dermatophytes, non-dermatophytes, yeasts and molds, are commonly found on the human foot and become airborne during these procedures. A preferred embodiment of the system for the podiatry industry is mountable to standard podiatric examination chairs. The connection between the system and the examination chair is advantageously detachable to allow the shield to be quickly detached to allow a patient to get in and out of the examination chair. FIG. 5 illustrates an example of a podiatric examination chair outfitted with a detachable shield 10.

Figure 6:
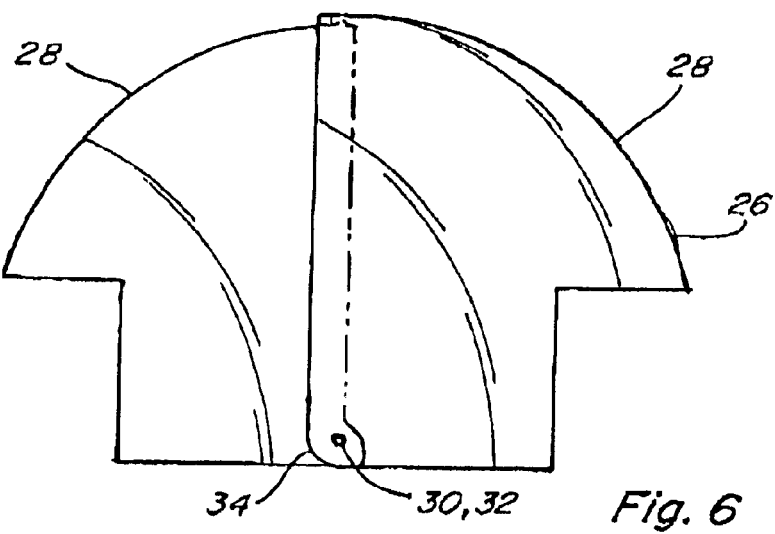
FIG. 6 is a schematic view of an airborne pathogen isolation system incorporating an adjustable shield.

The system will serve as a disposable, sterile shield used intra-operatively during surgery to protect the surgeon, surgical staff, and the patient from noxious fumes produced, for example, during hyfrucation and use of methyl metacrylate and potential exposure to blood and bodily fluids that are aerosolized during manual or power irrigation. The system will also reduce exposure to fumes and dust produced during procedures involving bone grinding, drilling or burring. As shown in FIG. 6, the system may include a shield 26 having a plurality of fan-shaped sections 28 that are connected by connection means 30. In the embodiment shown in FIG. 6, the sections 28 are connected by connection means 30 in the form of pins or bolts 32 at two pivot points 34, 36. The sections may be fanned out to varying degrees depending on the size and shape of the area to be isolated and then secured in that position by tightening the pins or bolts 32.

In the field of dentistry, high-speed drilling, irrigation, suction and smoke evacuation produce a variety of aerosolized particles and fume during dental procedures and the preparation of dental appliances and implants. The system would be used to isolate the dentist, hygienists, and the patient from these contaminants.

In addition, general use applications of the system in the home and variety of commercial settings include isolating the user from potential airborne pathogens produced, for example, during food preparation, use of art and craft supplies, and tooling and sanding jewelry.

Other objects, features and advantages of the present invention will be apparent to those skilled in the art. While preferred embodiments of the present invention have been illustrated and described, this has been by way of illustration and the invention should not be limited except as required by the scope of the appended claims and their equivalents.

What is claimed is:

1. An apparatus for isolating airborne pathogens created during a procedure performed on an individual's extremity, including:

a transparent, dome-shaped shield having first and second openings therein to allow two individuals to insert their respective extremities into the shield, said first and second openings being located on opposite sides of the shield, and said shield further having a ventilation opening;

a fan having an inlet and an outlet, said fan being mounted to the shield and communicating with the ventilation opening;

an air-cleaning filter located adjacent to the inlet of the fan, wherein the fan directs fumes created during the procedure through the filter; and a sleeve alternately and selectively mounted to said shield and communicating with the ventilation opening in place of at least said fan, said sleeve being operative for connection with a ventilation system.

2. An apparatus for isolating airborne pathogens as set forth in claim 1, wherein said ventilation opening is located generally between said first and second openings.

3. An apparatus for isolating airborne pathogens as set forth in claim 1, wherein the dome-shaped shield is vacuum-formed from polyethylene terephthalate glycol.

4. An apparatus for isolating airborne pathogens set forth in claim 1, wherein the air-cleaning filter is a high-efficiency particulate air filter.

5. An apparatus for isolating airborne pathogens as set forth in claim 1, wherein the fan is mounted to the exterior of the shield at the ventilation opening with the fan outlet oriented away from the ventilation opening and the filter is mounted to the interior of the shield at the ventilation opening.

6. An apparatus for isolating airborne pathogens as set forth in claim 1, wherein the filter and the fan are connected with one another forming a ventilation unit, said ventilation unit being mounted to the exterior of the shield at the ventilation opening.

7. An apparatus for isolating airborne pathogens as set forth in claim 1, wherein the shield includes a plurality of overlapping fan-shaped sections pivotably connected with one another.

8. An apparatus for isolating airborne pathogens as set forth in claim 1, further including a light fixture mounted to the shield.

9. An apparatus for isolating airborne pathogens as set forth in claim 1, wherein a direction of operation of the fan is reversible.

10. A method for isolating airborne pathogens created during a procedure on an individual's extremity, including the steps of:

inserting the individual's extremity into a transparent, dome-shaped shield having first and second openings and a ventilation opening, said extremity inserted through the first opening;

inserting a nail care tool into the shield through the second opening;

performing the procedure on the individual's extremity with the nail care tool;

selectively ventilating air from the interior of the shield with at least one of a fan connected with the shield at the ventilation opening and an exterior ventilation system connected with the shield at the ventilation opening by a sleeve; and filtering the air during ventilation with an air-cleaning filter.

11. A podiatric examination chair for isolating airborne pathogens created during a medical procedure on an individual's extremity, including:

a patient support portion having a seat, a back, and a leg support; and a transparent, dome-shaped shield detachably connected to the leg support and having first and second openings therein, wherein the individual's extremity is inserted into the interior of the shield through the first opening and a tool to perform the procedure is inserted into the shield through the second opening.

12. A podiatric examination chair for isolating airborne pathogens created during a medical procedure on an individual's extremity as set forth in claim 10, wherein the shield defines a ventilation opening and further including:

a fan having an inlet and an outlet, said fan being mounted to the shield and communicating with the ventilation opening; and an air-cleaning filter located adjacent to the inlet of the fan, wherein the fan directs fumes created during the procedure through the filter.

* * * * *